United States Patent
Kim et al.

(10) Patent No.: US 12,214,145 B2
(45) Date of Patent: Feb. 4, 2025

(54) CATHETER, COMPOSITION FOR CATHETER, PRODUCTION METHOD THEREFOR

(71) Applicant: AP MDS Co., Ltd., Incheon (KR)

(72) Inventors: Jong Jeong Kim, Incheon (KR); Yong Han Chun, Incheon (KR)

(73) Assignee: AP MDS Co., Ltd., Incheon (KR)

( * ) Notice: Subject to any disclaimer, the term of this patent is extended or adjusted under 35 U.S.C. 154(b) by 1062 days.

(21) Appl. No.: 16/991,435

(22) Filed: Aug. 12, 2020

(65) Prior Publication Data
US 2020/0368399 A1    Nov. 26, 2020

Related U.S. Application Data

(62) Division of application No. 16/068,173, filed as application No. PCT/KR2017/001138 on Feb. 2, 2017, now abandoned.

(30) Foreign Application Priority Data

Feb. 11, 2016  (KR) .................. 10-2016-0015702
Feb. 11, 2016  (KR) .................. 10-2016-0015711
(Continued)

(51) Int. Cl.
*A61M 25/10*     (2013.01)
*A61L 29/02*     (2006.01)
(Continued)

(52) U.S. Cl.
CPC ............. *A61M 25/10* (2013.01); *A61L 29/02* (2013.01); *A61L 29/06* (2013.01); *A61L 29/126* (2013.01);
(Continued)

(58) Field of Classification Search
CPC .............. A61M 25/10; A61M 25/0017; A61M 25/1075; A61M 25/0045; A61L 2400/12
See application file for complete search history.

(56) References Cited

U.S. PATENT DOCUMENTS 6,758,857 B2 *  7/2004  Cioanta .................. A61B 18/04
                                                                   604/113
8,017,684 B2    9/2011  Endo et al.
(Continued)

FOREIGN PATENT DOCUMENTS

CN    101724284 A    6/2010
CN    102202716 A    9/2011
(Continued)

OTHER PUBLICATIONS

K. Bharathi Yazhini et al., "Antibacterial Activity of Cotton Coated With ZnO", and ZnO—CNT Composites, Applied Biochemistry and Biotechnology, 2015, vol. 175, pp. 85-92.
(Continued)

*Primary Examiner* — Leslie R Deak
(74) *Attorney, Agent, or Firm* — Bridgeway IP Law Group, PLLC; Sang Ho Lee; Hyun Woo Shin

(57) ABSTRACT

Provided is foley catheter and a composition for producing a foley catheter which is inserted in vivo and a method for producing the same, which the composition consists of the materials which carbon nanotube polymer (CNT Polymer) bonded a carbon nanotube and zinc oxide (ZnO) is combined with a silicon, wherein from 1.0 to 2.2 parts by weight of the said carbon nanotube polymer are combined with 100 parts by weight of silicon.

18 Claims, 15 Drawing Sheets

(30) Foreign Application Priority Data

| | | | |
|---|---|---|---|
| Feb. 11, 2016 | (KR) | ........................ | 10-2016-0015841 |
| Jan. 31, 2017 | (KR) | ........................ | 10-2017-0013674 |
| Jan. 31, 2017 | (KR) | ........................ | 10-2017-0013677 |
| Jan. 31, 2017 | (KR) | ........................ | 10-2017-0013679 |

(51) Int. Cl.

| | |
|---|---|
| *A61L 29/06* | (2006.01) |
| *A61L 29/12* | (2006.01) |
| *A61L 29/16* | (2006.01) |
| *A61M 25/00* | (2006.01) |
| *C08G 77/58* | (2006.01) |
| *C08K 3/04* | (2006.01) |
| *C08K 3/22* | (2006.01) |
| *C08L 83/04* | (2006.01) |

(52) U.S. Cl.
CPC .......... *A61L 29/16* (2013.01); *A61M 25/0017* (2013.01); *C08G 77/58* (2013.01); *C08K 3/041* (2017.05); *C08K 3/22* (2013.01); *C08L 83/04* (2013.01); *A61L 2300/224* (2013.01); *A61L 2300/404* (2013.01); *A61L 2400/12* (2013.01); *A61M 2025/0056* (2013.01); *A61M 2025/1072* (2013.01); *C08K 2003/2296* (2013.01); *C08K 2201/011* (2013.01)

(56) References Cited

U.S. PATENT DOCUMENTS

| | | | |
|---|---|---|---|
| 8,673,441 B2 | 3/2014 | Cichos et al. | |
| 2007/0100279 A1* | 5/2007 | Bates | ................... A61L 29/126 |
| | | | 977/700 |
| 2007/0298669 A1 | 12/2007 | Barrera et al. | |
| 2009/0162643 A1* | 6/2009 | Dubrow | ................. A61P 35/00 |
| | | | 977/931 |
| 2015/0014577 A1 | 1/2015 | Chowdhury et al. | |
| 2015/0112228 A1 | 4/2015 | Ekema et al. | |
| 2019/0328563 A1* | 10/2019 | Boyle | ....................... A61F 2/91 |

FOREIGN PATENT DOCUMENTS

| | | | | |
|---|---|---|---|---|
| CN | 102639162 A | 8/2012 | | |
| CN | 102886077 A | 1/2013 | | |
| CN | 104225762 A | 12/2014 | | |
| CN | 104387655 A | 3/2015 | | |
| JP | 2005-511212 A | 4/2005 | | |
| JP | 2010-534729 A | 11/2010 | | |
| JP | 2010-537793 A | 12/2010 | | |
| JP | 2012-200274 A | 10/2012 | | |
| WO | WO-02064070 A1 * | 8/2002 | ............. | A61B 18/04 |

OTHER PUBLICATIONS

Minghao Sui et al., "Synthesis of ZnO coated multi-walled carbon nanotubes and their antibacterial activities", Science of the Total Environment, 2013, vols. 452-453, pp. 148-154.
Characteristics and Properties of Single and Multi Walled Carbon Nanotubes (webpage obtained from https://www.azonano.com/article.aspx?Articleid=1560).

* cited by examiner

| E. coli 3 day | (2016/02/29)(×1) | 570nm measured absorbance | | | average value | average P value |
|---|---|---|---|---|---|---|
| 0% | | 0.294 | 0.263 | 0.351 | 0.303 | 0.218 |
| 1% | | 0.349 | 0.264 | 0.364 | 0.326 | |
| 2% | | 0.233 | 0.231 | 0.293 | 0.252 | |
| 5% | | 0.240 | 0.315 | 0.342 | 0.299 | |

Fig. 3

| | E. coli 5 day | | (2016/03/02)(×1) | 570nm measured absorbance | | | average value | average P value |
|---|---|---|---|---|---|---|---|---|
| 0% | | | | 0.393 | 0.274 | 0.418 | 0.362 | 0.218 |
| 1% | | | | 0.416 | 0.306 | 0.417 | 0.380 | |
| 2% | | | | 0.368 | 0.310 | 0.390 | 0.356 | |
| 5% | | | | 0.492 | 0.445 | 0.407 | 0.448 | |

Fig. 4

| E. coli 7 day (2016/03/04)(×1) | | | 570nm measured absorbance | | | average value | average P value |
|---|---|---|---|---|---|---|---|
| 0% |    | | 0.530 | 0.507 | 0.422 | 0.486 | 0.333 |
| 1% |    | | 0.481 | 0.428 | 0.367 | 0.425 | |
| 2% |    | | 0.477 | 0.403 | 0.342 | 0.407 | |
| 5% |    | | 0.370 | 0.462 | 0.407 | 0.413 | |

CATHETER, COMPOSITION FOR CATHETER, PRODUCTION METHOD THEREFOR

CROSS-REFERENCE TO RELATED APPLICATIONS

This application is a divisional application of U.S. application Ser. No. 16/068,173 filed on Jul. 5, 2018, which is a national-stage application of international application No. PCT/KR2017/001138 filed on Feb. 2, 2017, and claims priority under 35 USC § 119 to Korean patent application Nos. 10-2016-0015702, 10-2016-0015711 and 10-2016-0015841 filed on Feb. 11, 2016, and Nos. 10-2017-0013674, 10-2017-0013677, 10-2017-0013679 filed on Jan. 31, 2017, the entire disclosures of which are incorporated herein by reference in their entirety.

BACKGROUND OF THE INVENTION

Field of the Invention

The present invention relates to a composition for producing a foley catheter which is inserted in vivo and a method for producing the same.

Description of the Prior Art

In general, patients with systemic or lower body paralysis caused by cerebral diseases such as stroke or spinal injuries are increasing year by year due to an increase in the elderly population and an increase rapidly in traffic accidents or industrial accidents.

A bladder paralysis is inevitably accompanied in such patients. A treatment of bladder paralysis is entirely dependent on the prognosis of the patient, and a foley catheter is maintained in the bladder as a treatment for these patients.

The foley catheter is made by attaching a foley to the distal end portion of the tubular catheter body so that the foley is expanded by the fluid introduced from the outside to have a balloon shape, which the catheter is held in the bladder.

In the case of a conventional antibiotic catheter, an antibiotic drug or a substance is applied to a foley catheter made of a silicone to suppress invasion of bacteria. Although antibiotics are initially effective in antibiotics, biofilm formation is occurred inevitably due to the intubation of the urinary tract for more than from 2 to 3 days according to the nature of the catheter.

Such biofilm formation may cause the antibiotic effect of the foley catheter to decrease or disappear so that there is a problem that the complications such as urinary tract infection is resulted and treatment for this should be accompanied and the length of hospital stay is prolonged.

In addition, since the antibiotic drugs or substances applied to the surface of the conventional foley catheter are always held in the fastening state, the urinary tact infections and stones are formed, resulting in kidney failure in 40% of the total patients, which is the greatest cause of death.

On the other hand, in order to solve the problems of the above-mentioned antibiotic catheter, there are some products coated with antibacterial materials such as gold, silver or silver nano. However, there has been a problem that the antibacterial activity is decreased due to peeling of the coated antibacterial substance when used over a certain period of time.

It should be understood that the inventive step of the present invention should not be judged based on the recognition for the problems and challenge of the prior art described above because such recognition is not obvious to those of ordinary skill in the art.

SUMMARY OF THE INVENTION

Accordingly, it is an object of the present invention to provide a composition for producing a foley catheter having an improved antibacterial property and being able to maintain its antibacterial property even for long-term use, and a method for producing the same.

According to an embodiment of the present invention, it is characterized in that the composition for producing the foley catheter which is inserted in vivo consists of a material which a carbon nanotube polymer (CNT Polymer) bonded a carbon nanotube and zinc oxide (ZnO) is combined with a silicon, wherein from 1.0 to 2.2 parts by weight of the said carbon nanotube polymer are combined with 100 parts by weight of silicon.

In a preferred embodiment of the present invention, it is characterized in that the said composition for the catheter foley is used to produce the foley for catheter being affixed to the catheter body to be inflatable by fluid externally introduced, and made of a material which a carbon nanotube polymer (CNT Polymer) bonded a carbon nanotube and zinc oxide (ZnO) is combined with a silicon, and from 4.0 to 13.2 parts by weight of the said carbon nanotube polymer are combined with 100 parts by weight of silicon.

According to an embodiment of the present invention, it is characterized in that the process for producing a foley catheter of the present invention comprises the step of composite combining the dispersed carbon nanotube and zinc oxide (ZnO) with silicon and then constituting the material which a carbon nanotube polymer (CNT Polymer) is combined to silicon.

Being constituting as the above, according to an embodiment of the present invention, a catheter body and a foley for catheter are made of a material which a carbon nanotube polymer (CNT Polymer) bonded a carbon nanotube and zinc oxide (ZnO) is combined with a silicon so that it is possible to inhibit the formation of a biofilm, which is the source of bacterial infection, without coating a separate antibiotic materials.

In addition, it has the effect of maintaining antibacterial property by inactivating the bacteria which is stenosed to the foley with keeping an induction of bio potential effect of the carbon nanotube polymer homogeneously.

In addition, the foley for catheter according to the present invention has no side effects such as resistance of antibiotics, and is characterized in that the lifetime of the carbon nanotube polymer is decided according to the amount of static electricity possessed by the said carbon nanotube polymer and the carbon nanotube polymer has high thermal conductivity so that it has the effect of minimizing the patient's rejecting feel during inserting process into a body and reducing the additional replacement cost and the increase of the medical expenses due to the infection.

The effects of the present invention described above are merely one of various effects according to the present invention, and the present invention can be realized in various forms according to the application mode of the embodiment.

BRIEF DESCRIPTION OF THE DRAWINGS

The combustion promoter according to the present invention will now be described by way of example only, with reference to the accompanying drawings, in which:

FIGS. 3 to 8 are diagrams showing experimental results on an effect for inhibiting a biofilm formation of the material constituting the foley catheter and the foley for catheter.

DETAILED DESCRIPTION OF THE INVENTION

Figure 1:
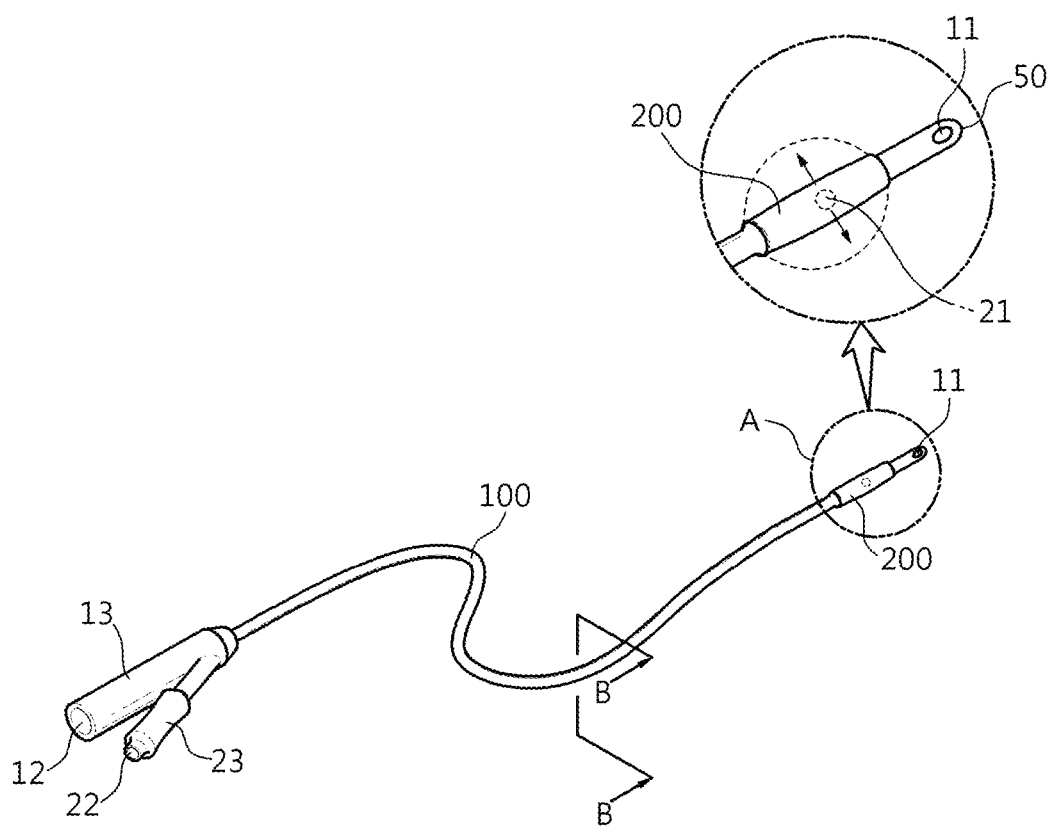
FIG. 1 is a perspective view showing a configuration of a foley catheter according to an embodiment of the present invention.

Hereinafter, a foley catheter, a foley for catheter and a method for producing the same according to the present invention will be described in further detail with reference to preferred embodiments. I is to be understood, however, that the scope of the present invention is not limited to these embodiments.

The foregoing objects, features and advantages of the present invention will become more apparent from the following detailed description taken in conjunction with the accompanying figures. Hereinafter, preferred embodiments of the present invention will be described in detail with reference to the accompanying figures. Like reference numerals designate like elements throughout the specification. Furthermore, in the following description, the well-known functions or constructions are not described in detail to avoid obscuring the subject matter of the present invention.

Figure 2:
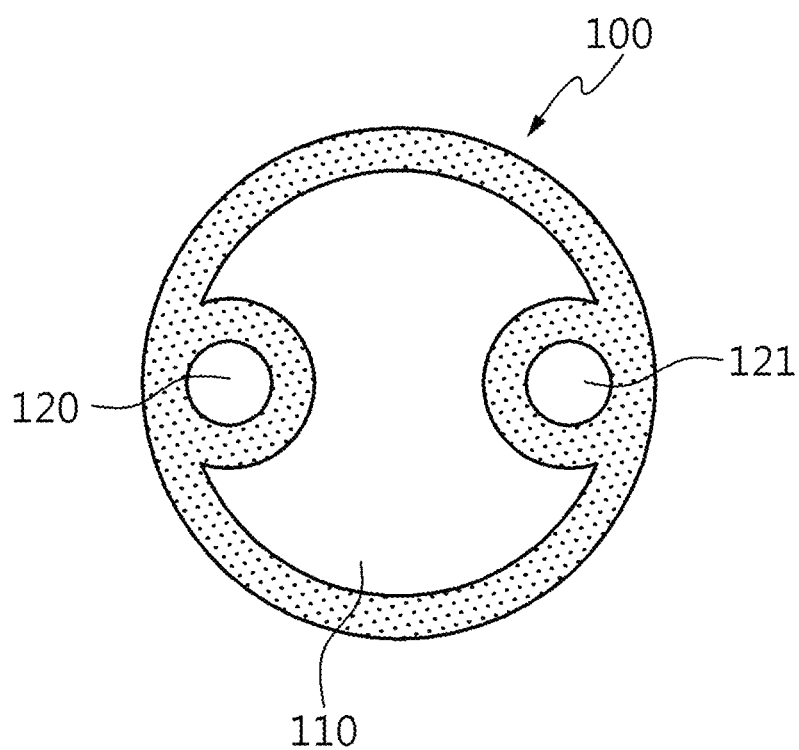
FIG. 2 is a cross sectional view showing an example of a cross sectional configuration of the foley catheter shown in FIG. 1.

FIG. 1 is a perspective view showing a configuration of a foley catheter according to an embodiment of the present invention, and FIG. 2 is a cross sectional view of a foley catheter taken along line B-B of FIG. 1 as an example of cross sectional constitution of a foley catheter.

A catheter according to an embodiment of the present invention may be a urine catheter for discharging urine in a bladder of a patient. A foley catheter may be constituted such that one side of catheter body is provided with a urine inlet and an inflatable foley, and a main tube positioned at the center of the catheter body communicates with a urine discharging part located on the other side of the catheter body to discharge urine in the bladder of the patient.

However, the catheter and the foley for catheter according to an embodiment of the present invention may be applied to various catheters such as a cardiovascular catheter in addition to the urethral catheter as described above.

Referring to FIGS. 1 and 2, the foley catheter comprises a catheter body 100 which is a tubular tube, and a foley for catheter 200 that is joined to the catheter body 100 to be inflatable by an externally introduced fluid.

More specifically, the inside of catheter body 100 may be formed with a urine passage 110 in which one end 50 is closed and urine moves and fluid passages 120 and 121 in which fluids move, respectively.

Furthermore, the urine inlet 11 is connected to the urine passage 110 of the catheter body 100 and the fluid outlet 21 may be connected to the fluid passages 120 and 121 of the catheter body 100.

Although FIG. 2 illustrates a catheter and a foley for catheter according to an embodiment of the present invention, for example, in which a catheter body 100 has one urine passage 110 and two fluid passages 120 and 121, the present invention is not limited thereto.

For example, one fluid passageway may be formed in the catheter body 100 and in case of a catheter of three-way mode rather than a two-way mode as shown in FIG. 1, a drug passage (not shown) may be additionally provided for introducing the medicine separately from the urine passage 110.

As being described above, the fluid passages 120 and 121 are connected to the fluid outlet 21 respectively so that fluid introduced from the outside through the fluid inlet 23 flows through the fluid passages 120 and 121 and the fluid outlet 21 and can be delivered to the jointed portion of the foley for catheter 200.

Here, said fluid may be a gas such as air or a liquid such as saline.

The foley 200 for catheter is composed of a material which may be expanded or contracted as the fluid flows in, and can be bonded to the catheter body 100 while surrounding the fluid outlet 21 formed in the catheter body 100.

The foley catheter and the foley for catheter according to an embodiment of the present invention having the structures described with reference to FIGS. 1 and 2 are made of a material which a carbon nanotube polymer (CNT polymer) is combined with a silicone, and it is possible to inhibit the formation of a biofilm which is the source of bacterial infection, without application or coating of antibiotics.

The carbon nanotubes (CNTs) are cylindrical crystals made of a carbon atom and have a diameter from 2 to 20 nm (1 nm being corresponding to 1/1,000,000 m) and a length from several hundred to several thousand nm. One carbon atom in the carbon nanotube forms a hexagonal honeycomb pattern by sp2 bonding with three other carbon atoms around it, which is called nanotube because the diameter of the tube is very small of about nanometers (nm).

Furthermore, the carbon nanotube polymer (CNT polymer) is a polymer in which carbon nanotubes (CNT) are bonded with zinc oxide (ZnO), and wherein carbon nanotubes (CNT) and zinc oxide (ZnO) can be polymerized at the same ratio from each other or zinc oxide (ZnO) can have a higher ratio than carbon nanotubes (CNT), and vice versa if necessary.

The catheter body 100 constituting the catheter according to an embodiment of the present invention may be consisted of materials which are blended 100 parts by weight of silicon with 1.0 to 2.2 parts by weight of carbon nanotube polymer, but the combining ratio may be variable.

According to the present invention, the carbon nanotube polymer as a component of the catheter body 100 has a constant capacitance in response to a potential in the intubated human body, so that such a capacitance is harmless to the human body, but has a galvanic effect which are deadly to bacteria and biofilms, which enable to minimizes the formation of biofilm, and the rejection of the subject during inserting process into the human body due to the high thermal conductivity which is characteristic of carbon nanotubes.

In addition, for the case of a catheter applied or coated with a conventional antibiotic, it is impossible to use the catheter for more than one week due to formation of biofilm and bacterial infection. But, the foley catheter according to the present invention can be used for at least 4 to 5 weeks due to the silicon which the carbon nanotube polymer (CNT polymer) having the above described effect is added.

According to an embodiment of the present invention, the carbon nanotube (CNT) may be a multi-walled carbon nanotube (MWNT) since the multi-walled carbon nanotube (MWNT) has a merit to use in a solid state and is likely to be commercialized in terms of price.

As being described above, the foley catheter and the foley for catheter according to an embodiment of the present invention may be consisted of material which a carbon nanotube polymer (CNT polymer) bonded carbon nanotubes (CNT) and zinc oxide (ZnO) as below chemical formula 1 is combined with a silicone respectively.

[Formula 1]

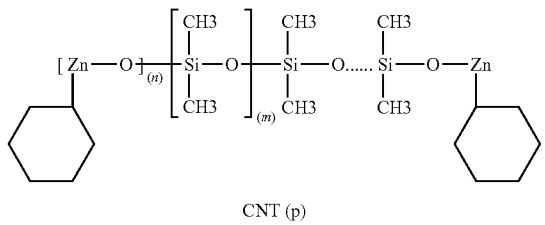

CNT (p)

In the above chemical formula (1), m, n and p represent the number of each of molecules of silicon, zinc oxide (ZnO) and carbon nanotube (CNT), m is 50 to 300, n is 7 to 30, and p is 10 to 50, but the present invention is not limited thereto.

On the other hand, in the catheter and the foley for catheter, the above m, n, and p may be set different from each other.

In addition, the catheter body 100 and the foley for catheter 200 for constituting the catheter according to an embodiment of the present invention may be a tubular tube obtained by extruding a carbon nanotube polymer (CNT) bonded carbon nanotube (CNT) and zinc oxide (ZnO) together with silicone in a predetermined ratio.

Herein, the above materials may be formed by compounding carbon nanotubes (CNT) and zinc oxide (ZnO) dispersed using a chemical vapor deposition (CVD) composite into silicon, for example, at a pressure of 1,000,000 Pa and a pressure of 50° C. for 30 minutes via dispersing process.

Accordingly, a carbon nanotube polymer composed of carbon nanotubes (CNT) and zinc oxide (ZnO) can be uniformly inserted into the silicon, whereby the catheter and the foley for catheter made of this material can have antibacterial activity uniformly with regardless of location.

Hereinafter, the effect for inhibiting formation of biofilm at the material constituting the foley catheter and the foley for catheter according to one embodiment of the present invention will be described with reference to FIGS. 3 to 8.

Figure 5:
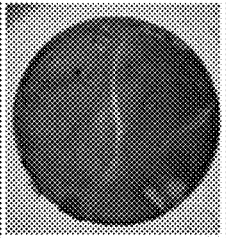
Figure 5:
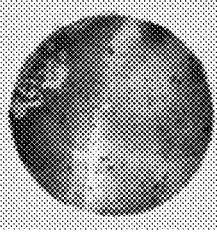
Figure 5:
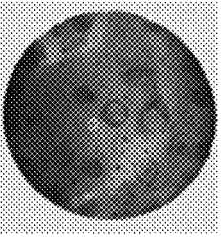
Figure 5:
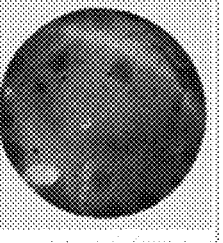
Figure 5:
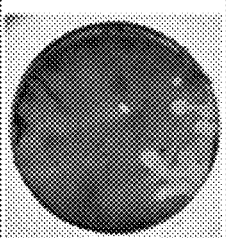
Figure 5:
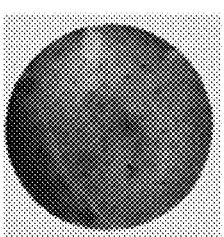
Figure 5:
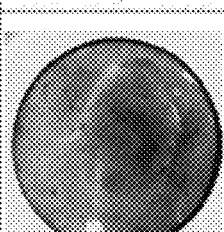
Figure 5:
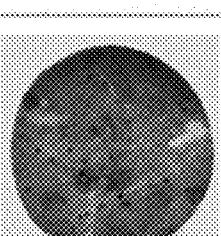
Figure 5:
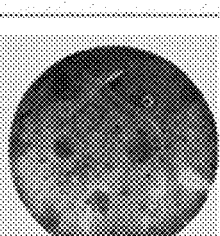
Figure 5:
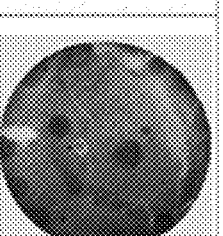
Figure 5:
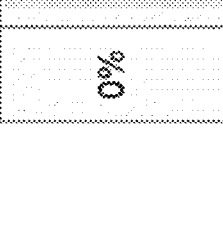
Figure 5:
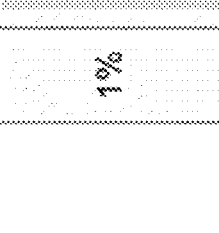

FIGS. 3 to 5 show the results obtained by culturing *E. coli* (*Escherichia coli.*) which is a major pathogen of urinary tract infection, on a catheter slice composed of the above materials for 3 days, 5 days, and 7 days, and experiment of forming degree of biofilm using the crystal violet method.

With reference to FIG. 3, when *E. coli* (*Escherichia coli*) was cultured for 3 days, the average value of absorbance was measured with 0.303 for the blending ratio of zinc oxide (ZnO) of 0%, the average value of absorbance was measured with 0.326 for the blending ratio of zinc oxide (ZnO) of 1%, the average value of absorbance was measured with 0.252 for the blending ratio of zinc oxide (ZnO) of 2%, and the average value of absorbance was measured with 0.299 for the blending ratio of zinc oxide (ZnO) of 3%.

With reference to FIG. 4, when *E. coli* (*Escherichia coli*) was cultured for 5 days, the average value of absorbance was measured with 0.362 for the blending ratio of zinc oxide (ZnO) of 0%, the average value of absorbance was measured with 0.380 for the blending ratio of zinc oxide (ZnO) of 1%, the average value of absorbance was measured with 0.356 for the blending ratio of zinc oxide (ZnO) of 2%, and the average value of absorbance was measured with 0.448 for the blending ratio of zinc oxide (ZnO) of 3%.

With reference to FIG. 5, when *E. coli* (*Escherichia coli*) was cultured for 7 days, the average value of absorbance was measured with 0.486 for the blending ratio of zinc oxide (ZnO) of 0%, the average value of absorbance was measured with 0.425 for the blending ratio of zinc oxide (ZnO) of 1%, the average value of absorbance was measured with 0.407 for the blending ratio of zinc oxide (ZnO) of 2%, and the average value of absorbance was measured with 0.413 for the blending ratio of zinc oxide (ZnO) of 3%.

Figure 6:
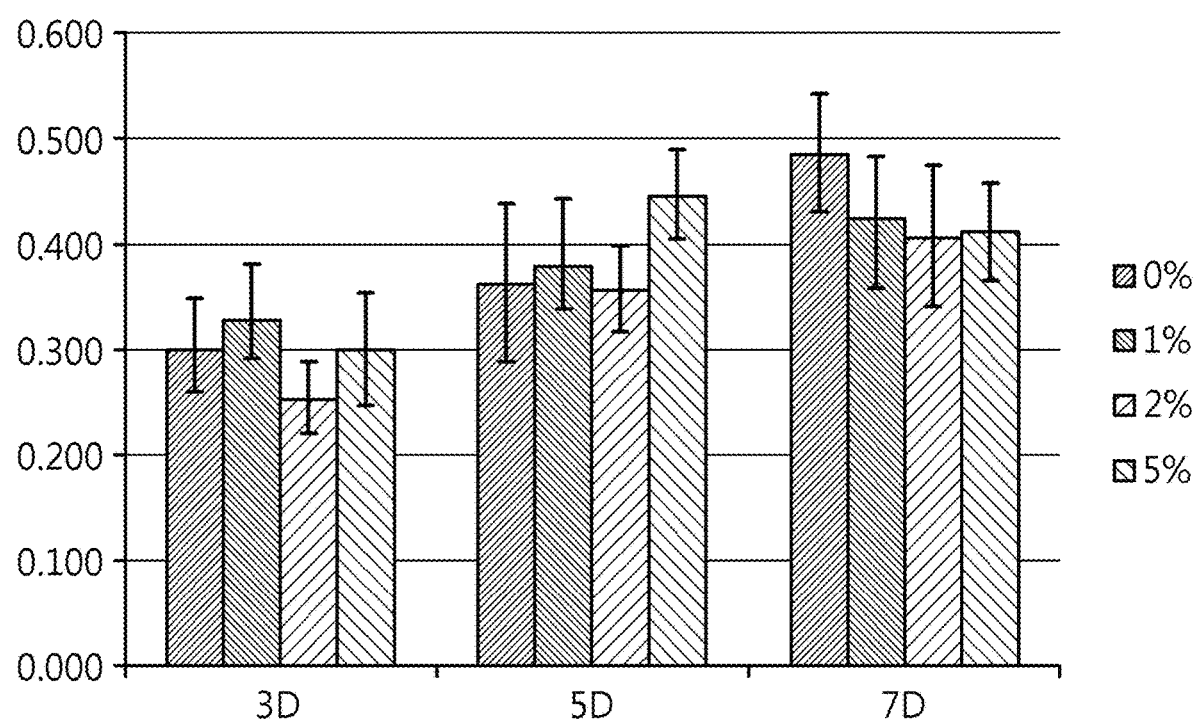
Figure 7:
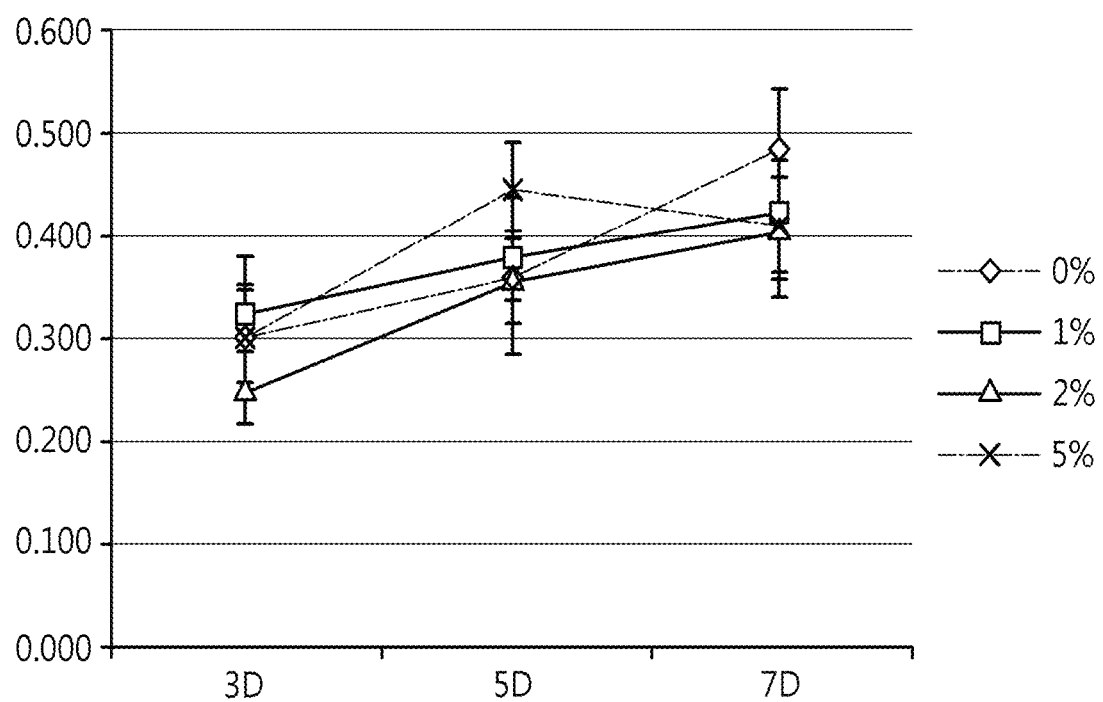

FIG. 6 is a graph showing the results of the experiment described above with respect to the experimental materials, and FIG. 7 is a graph showing the results of the experiments described above with respect to the culturing time.

According to the experimental results shown in FIG. 3 to 6, for a material in which the silicon and the carbon nanotubes (CN) are mixed with silicon (i.e. 0% of zinc oxide (ZnO)), the average value of absorbance is rapidly increased over time, thereby formation of the biofilm is increased.

On the other hand, for a material in which 1% of zinc oxide (ZnO) is mixed with silicon and carbon nanotube (CNT), the average value of absorbance is slowly increased than that in the case of a material in which the carbon nanotubes (CNT) are mixed with silicon (i.e. 0% of zinc oxide (ZnO)), thereby formation of the biofilm is suppressed to some extent.

In addition, for a material in which 2% of zinc oxide (ZnO) is mixed with silicon and carbon nanotube (CNT), the average value of absorbance is generally lower than that in the case of a material in which the carbon nanotubes (CNT) are mixed with silicon (i.e. 0% of zinc oxide (ZnO)) and 1% of zinc oxide (ZnO) is mixed with silicon and carbon nanotube (CNT), thereby the inhibitory effect on the biofilm formation of a major strain of urinary tract infection, *E. coli*(*Escherichia coli.*) is clearly shown.

And, for material in which 5% of zinc oxide (ZnO) is mixed with silicon and carbon nanotube (CNT), the average value of absorbance after 7 days of culture was lower than before, resulting in an effect for inhibiting a biofilm formation according to use of long period of time.

Based on the above experimental results, when a catheter and a foley for catheter are composed of silicon and carbon nanotube (CNT) in which zinc oxide (ZnO) is blended with about 2%, an inhibitory effect on the biofilm formation of a major strain of urinary tract infection, *E. coli* (*Escherichia coli.*) can be stably achieved.

Figure 8:
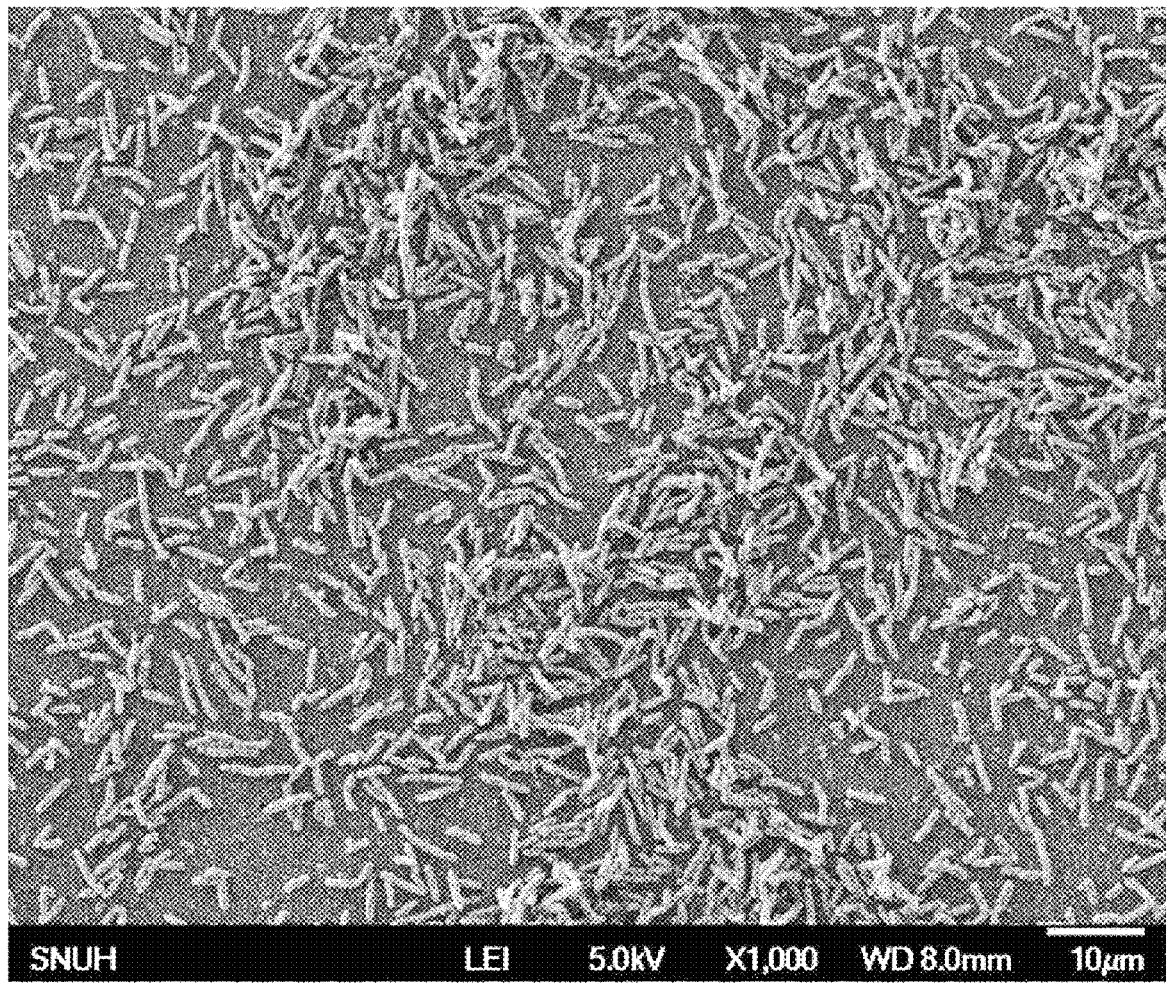

FIG. 8 is a photograph of the results obtained by culturing *E. coli* (*Escherchia coli*) in a material having a zinc oxide (ZnO) blending ratio of 1% for 7 days and then taking the results of the experiment with a scanning electron microscope (SEM).

With reference to FIG. 8, even after 7 days of culture, it can be seen that the microorganisms, *E. coli* do not form a biofilm by aggregation.

Also, referring to the experimental results shown in Table 1 below, the material constituting the catheter and the foley for catheter according to an embodiment of the present invention have a bactericidal reduction rate of more than 99.9% and a bacteriostatic reduction rate for *Staphylococcus aureus*, pneumococcus, *Escherichia coli* and *Pseudomonas aeruginosa* in addition to said *E. coli*.

TABLE 1

| NO | Initial vaccination | 24 hours | Proliferation value (F) | Bactericidal reduction rate (%) | Bacteriostatic reduction rate (%) | Sample name |
|---|---|---|---|---|---|---|
| *Staphylococcus aureus* (CFU/ml) | | | | | | |
| 1 | 3.1E+04 | 1.7E+06 | 55 | — | — | SD BLANK |
| 2 | | 1.0E+01 | | 99.97% | 99.99% | |
| 3 | | 1.0E+01 | | 99.97% | 99.99% | ZnO 15 |
| *Pneumococcus* (CFU/ml) | | | | | | |
| 1 | 2.2E+04 | 3.0E+06 | 136 | — | — | SD BLANK |
| 2 | | 1.0E+01 | | 99.95% | 99.99% | |
| 3 | | 1.0E+01 | | 99.95% | 99.99% | ZnO 15 |
| *Escherichia coli* (CFU/ml) | | | | | | |
| 1 | 2.1E+04 | 1.8E+06 | 86 | — | — | SD BLANK |
| 2 | | 1.0E+01 | | 99.95% | 99.99% | |
| 3 | | 1.0E+01 | | 99.95% | 99.99% | ZnO 15 |
| *Pseudomonas aeruginosa* (CFU/ml) | | | | | | |
| 1 | 1.2E+04 | 1.8E+06 | 150 | — | — | SD BLANK |
| 2 | | 1.0E+01 | | 99.92% | 99.99% | |
| 3 | | 1.0E+01 | | 99.92% | 99.99% | ZnO 15 |

On the other hand, the catheter and the foley for catheter configured as described above can minimize the patient's rejection feeling in the process of inserting the human body due to the high heat conduction characteristic of the carbon nanotube.

Figure 9:
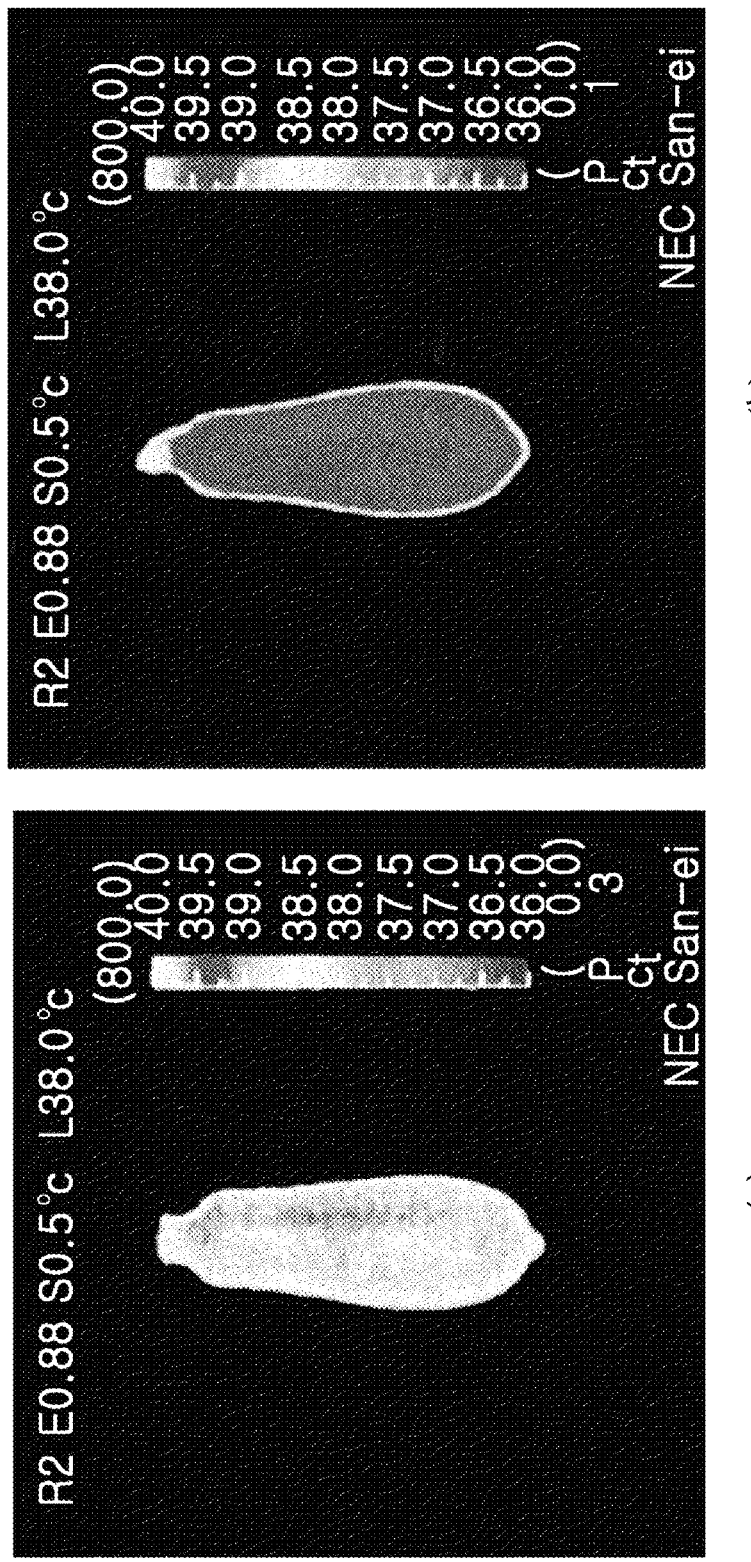
FIG. 9 is a view showing experimental results for explaining an effect of reducing the foreign sensation when the materials constituting a foley catheter and a foley for catheter are inserted into the human body.

FIG. 9 is view showing experimental results for explaining an effect of reducing the foreign sensation when the materials constituting a foley catheter and a foley for catheter are inserted into the human body. FIG. 9 (*a*) is a thermal image of a catheter made of silicon in which carbon nanotubes do not internalized, and FIG. 9 (*b*) is a thermal image of a catheter made of silicon in which carbon nanotubes are internalized.

With reference to FIGS. 9 (*a*) and 9 (*b*), it can be seen that the temperature distribution is uniform due to the high thermal conductivity in the case of a catheter composed of silicon in which carbon nanotubes are internalized.

Figure 10:
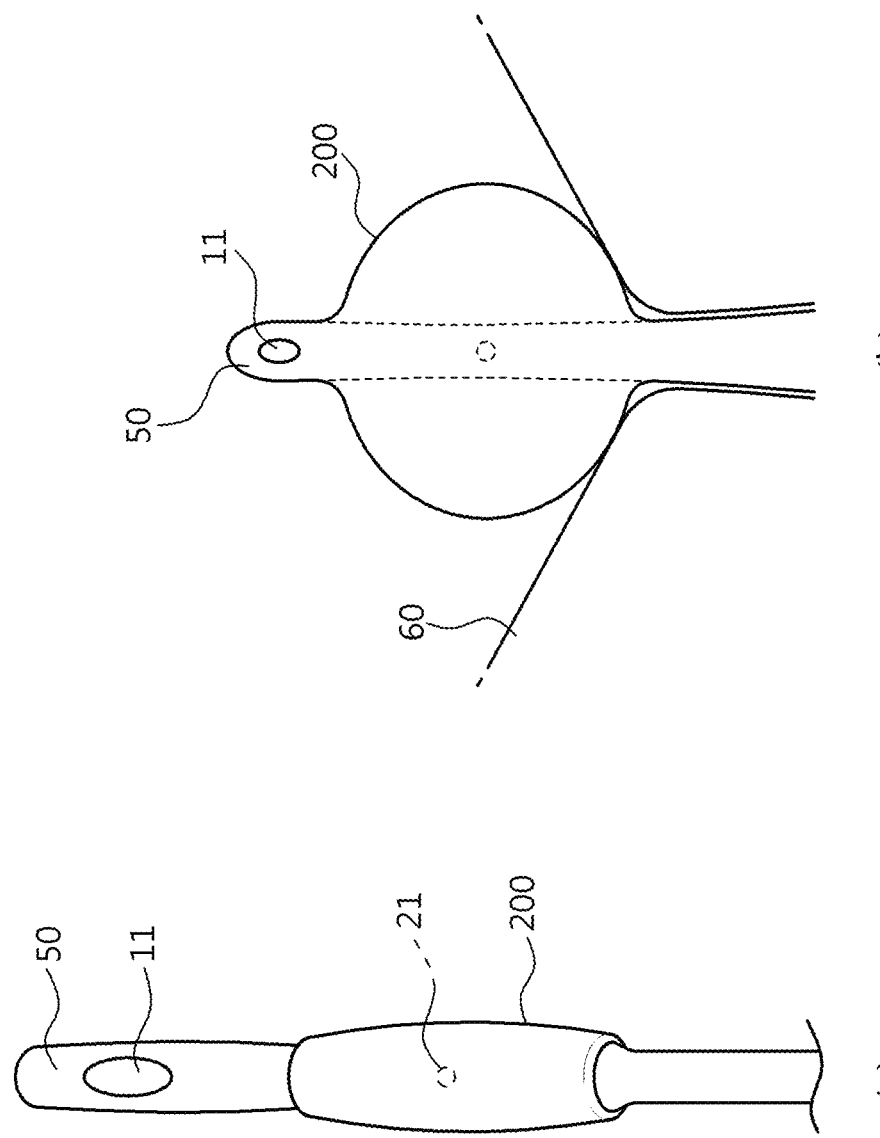
FIG. 10 is a drawing for explaining the configuration and operation of a foley for catheter according to an embodiment of the present invention.

FIG. 10 is a drawing for explaining the configuration and operation of a foley for catheter according to an embodiment of the present invention. The descriptions for the same components as those described with reference to FIGS. 1 to 9 will be omitted herein.

Referring to FIG. 10, a catheter body 100 is formed with a urine inlet 11 and a foley for catheter 200 adjacent one end 50 of the foley for catheter that is inserted into the bladder.

The foley for catheter 200 may expand to form a balloon when fluid (e.g., air or saline) is introduced from the fluid inlet 23 provided on the other side of the catheter.

For example, a fluid may be introduced in a manner such that a fluid is previously injected into a syringe, the syringe needle is inserted into the inflow hole 22 at the end of the fluid inflow portion 23, and the syringe is compressed.

A foley for catheter 200 configured to abut one end 50 of the catheter body 100 is inserted into the bladder, and at that state, the fluids flow from the fluid inlet 23 through the fluid passages 120 and 121 and the fluid outlet 21 into the foley for catheter 200, thereby the foley for catheter 200 bulges in a balloon shape and spans the bladder neck 60 to secure the catheter within the bladder.

On the other hand, a urine passage 110 connected to the urine inlet 11 is formed at the center of a cross section of the catheter body 100 and a urine outlet 13 is formed at the end of the urine passage 110.

For example, the urine generated in the urethra is introduced into the urine passage 110 through the urine inlet 11 located in the urethra, and then discharged via the urine outlet 12, which is the end of the urine discharging portion 13 located at outside of the urethra.

Figure 11:
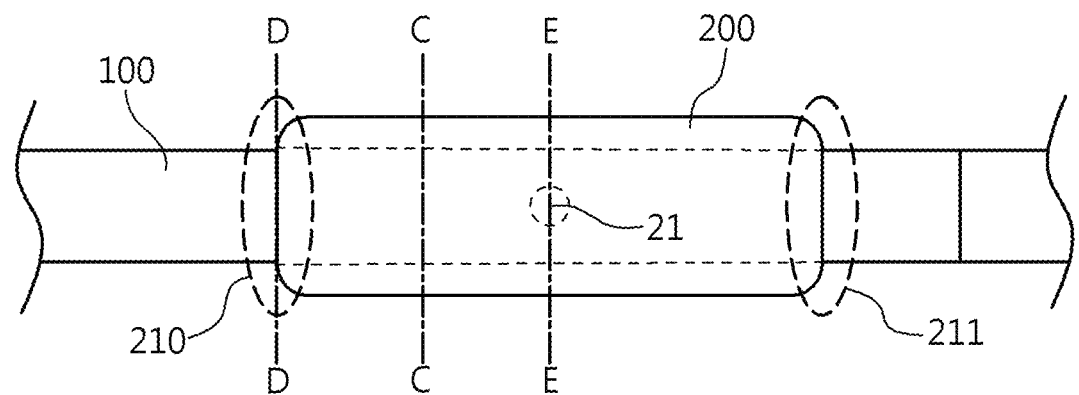
FIG. 11 is a drawing showing one embodiment of the configuration of a foley for catheter according to the present invention in more detail.

FIG. 11 shows a drawing showing one embodiment of the configuration of a foley for catheter according to the present invention in more detail, and specifically an enlarged representation of the portion of the foley for catheter 200 shown in FIGS. 1 and 11 where it is joined.

Referring to FIG. 11, bonding surfaces 210 and 211 are formed at both ends of the foley for catheter 200 to be joined to the catheter body 100 and bonding surfaces 210 and 211 may be bonded to the catheter body 100 using an adhesive during process forming the foley for catheter 200 at the catheter body 100.

Hereinafter, a method of manufacturing a foley catheter and a method of forming a foley for catheter according to an embodiment of the present invention will be described with reference to FIG. 11.

First, as being described above, a carbon nanotube polymer (CNT polymer) in which carbon nanotubes and zinc oxide (ZnO) are bonded is combined with a silicone and then is extruded into a tubular tube to form a catheter body 100.

In addition, a carbon nanotube polymer (CNT polymer) in which carbon nanotubes and zinc oxide (ZnO) are bonded is combined with a silicone and then is extruded or molded into a tubular tube to form a foley for catheter 200.

Herein, the mixing ratio of the carbon nanotube, zinc oxide (ZnO), or carbon nanotube polymer as a raw material for producing the catheter body 100 and the mixing ratio of the carbon nanotube, zinc oxide (ZnO) or a carbon nanotube polymer as a raw material for producing the foley for catheter 200 may be different.

For example, when the foley for catheter 200 is inflated by the fluid introduced from the outside, the surface area is increased, and the distribution of the carbon nanotube polymer per unit area is decreased, and the antibacterial ability may be lowered.

As being described above, if the foley for catheter 200 is inflated and the antibacterial ability is lowered, even if formation of biofilm is suppressed in the catheter body 100, biofilm is formed in the foley for catheter 200 which the antibacterial ability was lowered and then may cause bacterial infection.

According to one embodiment of the present invention, the combining ratio of the carbon nanotube polymer in the foley for catheter 200 is preferably higher than that of the carbon nanotube polymer in the catheter body 100. Therefore, the distribution of the carbon nanotube polymer per unit area has the same or similar range as that of the catheter body 100 even when inflated, so that a uniform infectious power can be maintained regardless of the position of the foley for catheter 200.

Assuming that the foley for catheter 200 expands to increase the surface area by about 4 to 6 times, as being described above, when the catheter body 100 is formed of a material mixed with 1.0 to 2.2 parts by weight of carbon nanotube polymer relative to 100 parts by weight of silicon, the foley for catheter 200 may be composed of a material blended with 4.0 to 13.2 parts by weight of carbon nanotube polymer relative to 100 parts by weight of silicone in proportion to an increase in surface area.

On the other hand, for the foley for catheter 200, it may be preferable that the values of n and m in the chemical formula 1 increase in proportion to the increase in surface area upon expansion of the foley for catheter 200.

After the catheter body 100 and the foley for catheter 200 are prepared, bonding surfaces 210 and 211 of the foley for catheter 200 are attached to the catheter body 100 and the foley catheter can be manufactured by forming a tip provided with an urine inlet 11 at one end of the catheter body 100.

The method of manufacturing a foley catheter and the method of forming a foley for a catheter according to an embodiment of the present invention may further include additional steps such as a drying step in addition to the steps described above and a separate step may be added.

FIGS. 12 to 16 are cross-sectional views showing examples of the cross sectional configuration of a foley for catheter shown in FIG. 11.

Figure 12:
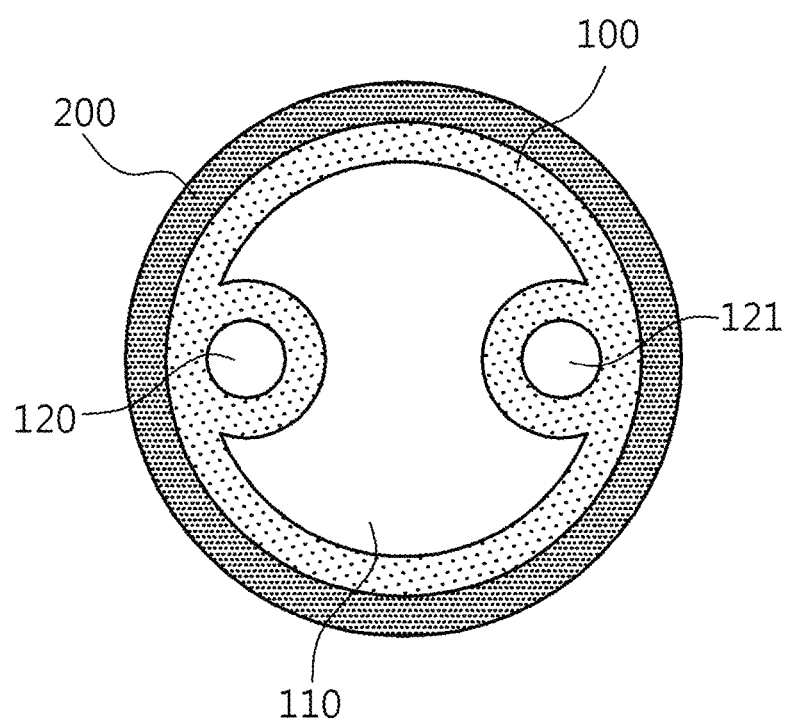
FIG. 12 to 16 are cross-sectional views showing examples of the cross sectional configuration of a foley for catheter shown in FIG. 11.

FIG. 12 is a cross-sectional view taken along the C-C line shown in FIG. 11, showing a structure in which the foley for catheter 200 covers the catheter body 100 having the urine passage 110 and the fluid passages 120 and 121.

Herein, when the foley for catheter 200 is manufactured using a material having a higher mixing ratio of the carbon nanotube polymer than the catheter body 100 as being described above, the current can flow until the potential difference is no longer present between the catheter body 100 shown in FIG. 12 and the foley for catheter 200.

This is because zinc oxide (ZnO) creates a high electrical potential and current flow from the foley for catheter 200 to the catheter body 100 at the abutting portion each other. When the potential difference is lost between the catheter body 100 and the foley for catheter 200, when the foley for catheter 200 is expanded, the electrostatic capacity is lowered and the antibacterial power may be decreased.

Figure 13:
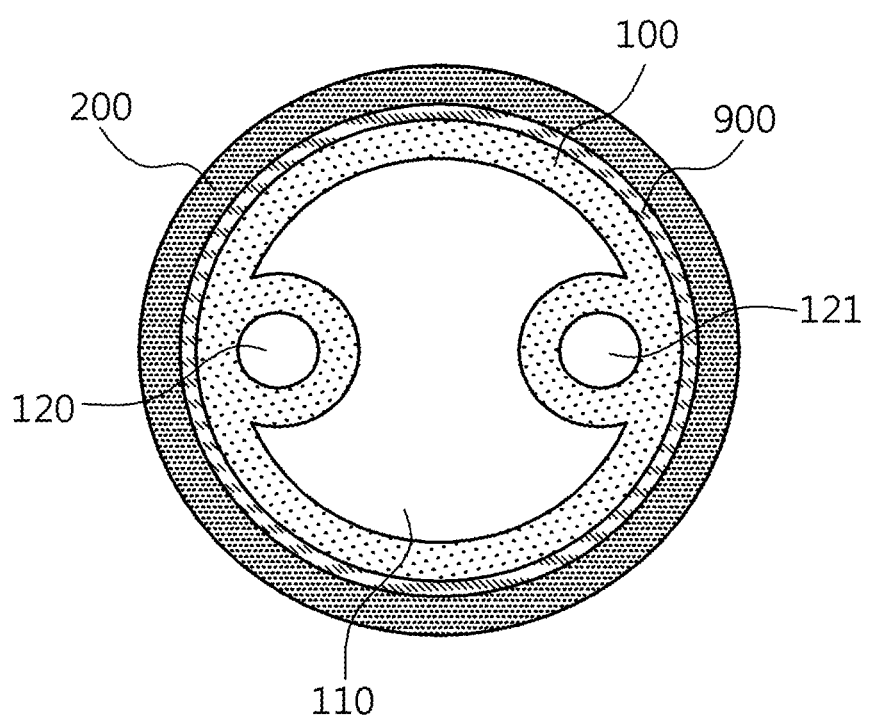

An insulating layer 900 is interposed between the catheter body 100 and the foley for catheter 200 as shown in FIG. 13 to prevent current from flowing from the foley for catheter 200 to the catheter body 100.

The insulating layer 900 may be composed of a gas such as an air layer or a sterilizing gas layer (for example, EO gas), or a carbon nanotube coating layer having a high concentration.

By preventing the electric current from flowing from the foley for catheter 200 to the catheter body 100 by the insulating layer 900, a potential difference due to the difference in the mixing ratio of the carbon nanotube polymer can be maintained, thereby the antibacterial power can be maintained in the same or similar range as the catheter body 100 even when the foley for catheter 200 is inflated.

As being shown at FIG. 13, the air layer is injected into between catheter body 100 and the foley for catheter 200 or an EO gas treatment or a high concentration carbon nanotube coating may be further applied to the outer surface of the catheter body 100 during the formation of the foley for catheter 200 so that an insulating layer 900 is formed between the catheter body 100 and the foley for catheter 200.

Figure 14:
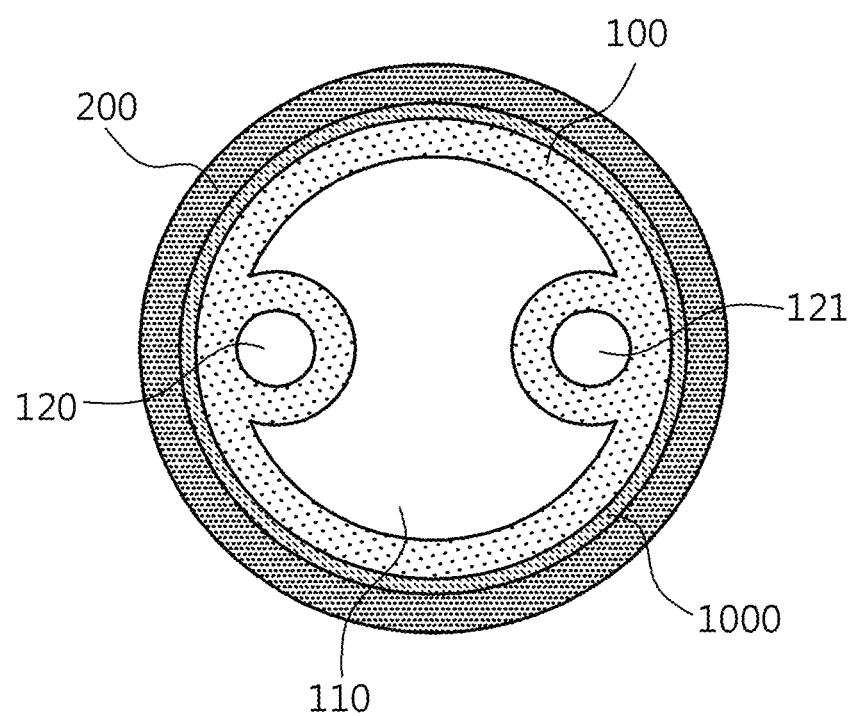

FIG. 14 is a cross-sectional view taken along the line D-D shown in FIG. 11, showing a cross-sectional structure of a portion of bonding surface 210 where the foley for catheter 200 is bonded to the catheter body 100.

Referring to FIG. 14, an insulating film 1000 may be formed on a bonding surface 210 where the foley for catheter 200 is bonded to the catheter body 100.

This is because when the adhesive used to bond the bonding surface 210 of the foley for catheter 200 to the catheter body 100 is conductive, the potential difference due to the difference in the mixing ratio of the carbon nanotube polymer causes the junction surface 210 since the current can flow from the foley for catheter 200 to the catheter body 100 through the insulating film 1000.

For example, the insulating film 1000 may be formed by coating a high concentration carbon nanotube on the bonding surface 210 as a carbon nanotube insulating film, and when the foley for catheter 200 is inflated, it may be dismantled naturally by increase of a surface area.

The insulating film 1000 as shown in FIG. 14 is also preferably applied to a cardiovascular catheter.

Figure 15:
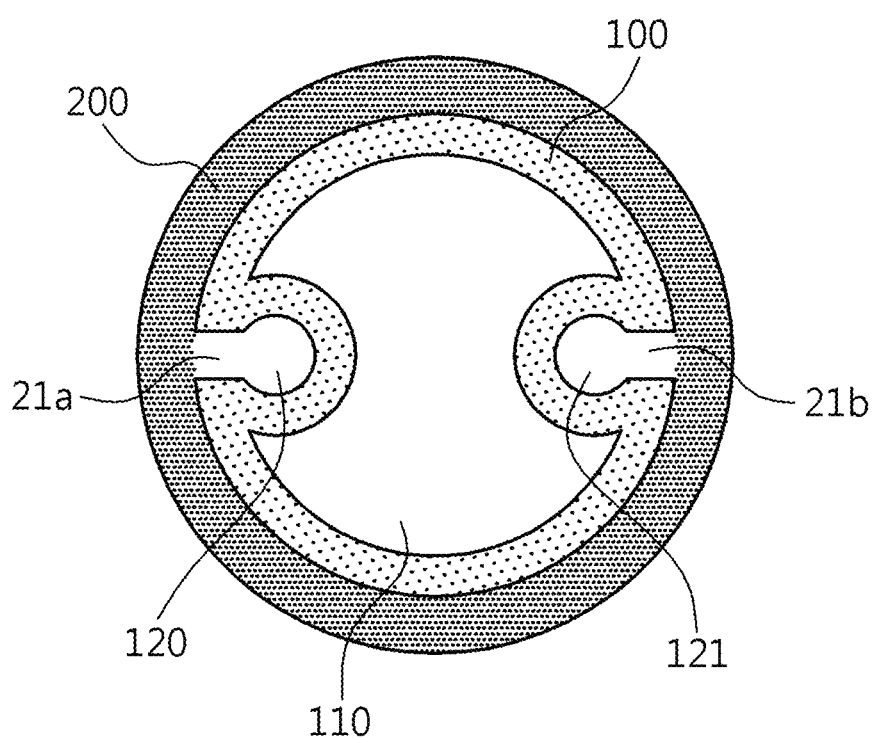

FIG. 15 is a cross-sectional view taken along the line E-E shown in FIG. 11, showing a cross-sectional structure of a portion where the fluid outlet 21 is formed.

Referring to FIG. 15, fluid outlets 21a and 21b may be formed at the corresponding positions communicated to the two fluid passages 120 and 121 formed in the catheter body 100, respectively.

Thereby, the fluid introduced from the outside flows through the fluid passages 120 and 121 of the catheter body 100 and then flows out through the fluid outlets 21a and 21b to the foley for catheter 200, and then the foley for catheter 200 is expanded by the pressure of the fluid.

Figure 16:
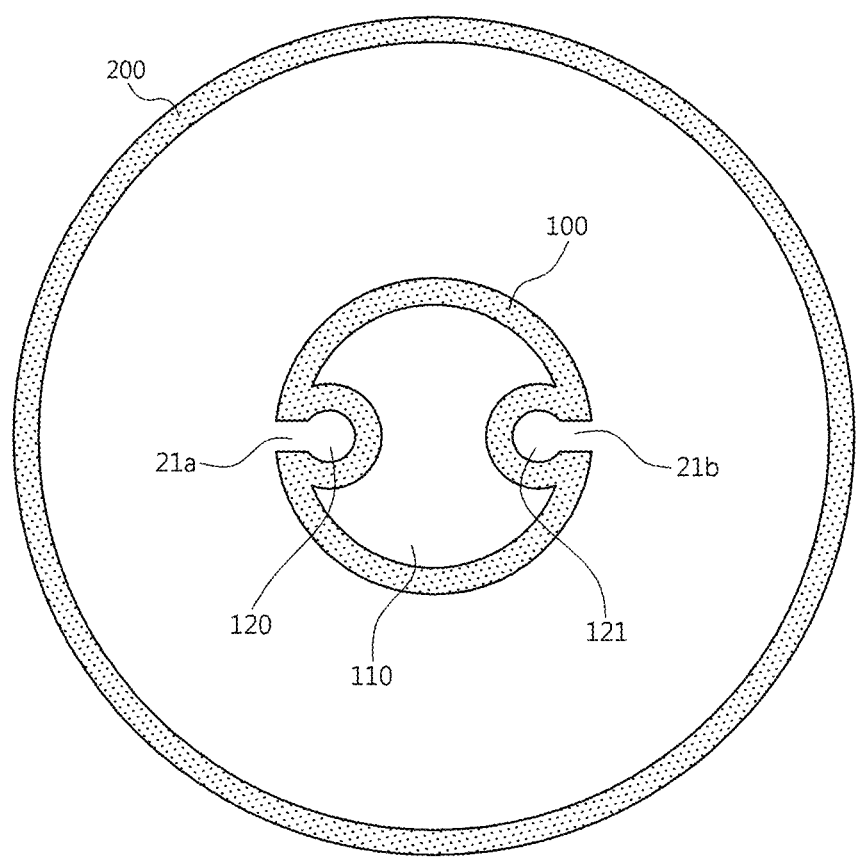

FIG. 16 is a cross-sectional view illustrating the expanded state of the foley for catheter 200.

Referring to FIG. 16, by increasing the blending ratio of the carbon nanotube polymer of the foley for catheter 200 to the ratio of the surface area increase rate during expansion to be larger than the blending ratio of the carbon nanotube polymer of the catheter body 100, the electrostatic capacity of the foley for catheter 200 may be kept the same or similar to that of the catheter body 100 when expanding so that the antibacterial power of the foley catheter can be uniform.

Although not shown separately in the drawings, the steps according to the manufacturing method may be added or reduced depending on the type or function of the catheter or the foley for catheter according to the present invention.

Although the present invention has been particularly shown and described with reference to exemplary embodiments thereof for illustrative purposes, it is clearly understood that the same is by way of illustration and example only and is not to be construed to the preferred embodiments of the present invention, and that various modifications, additions and substitutions are possible, without departing from the scope and spirit of the invention as disclosed in the accompanied claims.

What is claimed is:

1. A foley catheter comprising:
    a catheter body made of a first material comprising a first carbon nanotube polymer mixed with silicon;
    wherein the catheter body is formed as a single layer with at least one fluid passage,
    a foley balloon connected to the catheter body and configured to be inflated by a fluid introduced from outside, wherein the foley balloon is made of a second material comprising a second carbon nanotube polymer mixed with silicon, and
    an insulating layer disposed solely between the catheter body and the foley balloon, the insulating layer configured to prevent electric current from flowing from the foley balloon to the catheter body,
    wherein the first and second carbon nanotube polymers are polymerized with carbon nanotube and zinc oxide (ZnO), and
    wherein the second material has a higher mixing ratio of the second carbon nanotube polymer than the first carbon nanotube polymer, and there is an electrical potential difference between the foley balloon and the catheter body.

2. The foley catheter of claim 1, wherein the insulating layer is an air layer or a sterilizing gas layer.

3. The foley catheter of claim 1, wherein the insulating layer is a carbon nanotube coating layer.

4. The foley catheter of claim 1, wherein the first material comprises 1.0 to 2.2 parts by weight of the carbon nanotube polymer relative to 100 parts by weight of the silicon.

5. The foley catheter of claim 1, wherein the second material comprises 4.0 to 13.2 parts by weight of the carbon nanotube polymer relative to 100 parts by weight of the silicon.

6. The foley catheter of claim 1, wherein the mixing ratio of carbon nanotube polymer of the foley balloon for catheter is 4 to 6 times that of the mixing ratio of the carbon nanotube polymer of the catheter body.

7. The foley for catheter of claim 1, wherein an insulating film is disposed on a bonding surface where the foley balloon is connected to the catheter body.

8. The foley for catheter of claim 1, wherein the first and second carbon nanotube polymers are a multi-walled carbon nanotube.

9. The foley for catheter of claim 1, wherein the foley balloon is disposed to surround the catheter body and has a first end and a second end, an insulating film is interposed between the foley balloon and the catheter at the first end and the second end of the foley balloon, and the insulating layer is only disposed on at least part of the catheter body that corresponds to the foley balloon between the first end and the second end.

10. The foley for catheter of claim 9, wherein the catheter body that does not correspond to the foley balloon does not include either the insulating film or the insulating layer.

11. The foley for catheter of claim 1, wherein the foley balloon is disposed to surround the catheter body and has a first end and a second end, and the insulating layer is only disposed on at least part of the catheter body that corresponds to the foley balloon between the first end and the second end.

12. The foley for catheter of claim 1, wherein the catheter body that does not correspond to the foley balloon does not include the insulating layer.

13. The foley for catheter of claim 1, wherein the insulating layer has single layer entirely surrounding the catheter body.

14. A method for manufacturing a foley catheter, the method comprising:
    producing a catheter body by extruding a first material comprising a first carbon nanotube polymer mixed with silicon;
    producing a foley balloon by extruding or injecting a second material comprising a second carbon nanotube polymer mixed with silicon; and
    affixing the foley balloon to the catheter body and forming an insulating layer between the catheter body and the foley balloon,
    wherein the insulating layer is configured to prevent electric current from flowing from the foley balloon to the catheter body,
    wherein the foley balloon is connected to the catheter body and is configured be inflated by a fluid introduced from outside, and
    wherein the first and second carbon nanotube polymers are polymerized with carbon nanotube zinc oxide (ZnO), and the second material has a higher mixing ratio of the second carbon nanotube polymer than the first carbon nanotube polymer, and there is an electrical potential difference between the foley balloon and the catheter body.

15. The method of claim 14, wherein the insulating layer is an air layer or a sterilizing gas layer.

16. The method of claim 14, wherein the insulating layer is formed by gas sterilizing at an outer surface of the catheter body.

17. The method of claim 14, wherein the insulating layer is formed by coating carbon nanotube at an outer surface of the catheter body.

18. The method of claim 14, further comprising forming an insulating film on a bonding surface where the foley balloon for catheter is connected to the catheter body.

* * * * *